US012642533B2

(12) United States Patent
Ortiz Garcia et al.

(10) Patent No.: US 12,642,533 B2
(45) Date of Patent: Jun. 2, 2026

(54) LOCKING FEATURE FOR HEMOSTASIS CLIP

(71) Applicant: BOSTON SCIENTIFIC SCIMED, INC., Maple Grove, MN (US)

(72) Inventors: Juan Pablo Ortiz Garcia, Heredia (CR); Joseph W. King, Franklin, MA (US); Matthew Robert Jagelski, Milford, MA (US); Jimena Cespedes Berrocal, Alajuela (CR); Cristian Araya Camacho, Alajuela (CR); Gonzalo Jose Saenz Villalobos, Alajuela (CR); Robb Morse Gavalis, Westborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 546 days.

(21) Appl. No.: 18/163,734

(22) Filed: Feb. 2, 2023

(65) Prior Publication Data

US 2023/0248370 A1      Aug. 10, 2023

Related U.S. Application Data

(60) Provisional application No. 63/267,758, filed on Feb. 9, 2022.

(51) Int. Cl.
*A61B 17/122* (2006.01)
*A61B 17/12* (2006.01)
*A61B 17/128* (2006.01)

(52) U.S. Cl.
CPC ........ *A61B 17/122* (2013.01); *A61B 17/1285* (2013.01); *A61B 2017/12004* (2013.01)

(58) Field of Classification Search
CPC .............. A61B 17/122; A61B 17/1285; A61B 2017/12004; A61B 17/10; A61B 17/083
See application file for complete search history.

(56) References Cited

U.S. PATENT DOCUMENTS

2004/0236355 A1* 11/2004 Anthony ................ A61B 17/10
                                                        606/142
2005/0143767 A1*  6/2005 Kimura .................. A61B 50/30
                                                        606/158

(Continued)

FOREIGN PATENT DOCUMENTS

CA          3 156 896 A1      5/2021

*Primary Examiner* — Brooke Labranche
*Assistant Examiner* — Rachael L Geiger
(74) *Attorney, Agent, or Firm* — Fay Kaplun & Marcin, LLP

(57) ABSTRACT

A clipping system includes a clip, a core member and a control member.
The clip includes a capsule extending longitudinally from a proximal end to a distal end and including a channel extending therethrough, and clip arms. Proximal ends of the arms are slidably received within the channel to move the arms between open and closed configurations. The core member is received between and connected to the proximal ends of the arms to couple the arms to one another. The core member includes a locking feature movable between unlocked and locked configurations. The control member extends through a proximal portion of the system from a proximal end to an enlarged distal end housed within a proximal portion of the core member so that a longitudinal movement of the control member relative to the capsule moves the clip between the open and closed configurations.

20 Claims, 9 Drawing Sheets

(56)     References Cited

U.S. PATENT DOCUMENTS

2008/0306491 A1*  12/2008  Cohen ................ A61B 17/1285
                                          606/151
2019/0223875 A1*   7/2019  Saenz Villalobos ........................
                                          A61B 17/122
2019/0231353 A1*   8/2019  Saenz Villalobos ........................
                                          A61B 17/122
2020/0155159 A1*   5/2020  Murray ................ A61B 17/122
2020/0397436 A1    12/2020  Solano Montenegro et al.
2021/0022742 A1*   1/2021  Lehtinen ............ A61B 17/1227

* cited by examiner

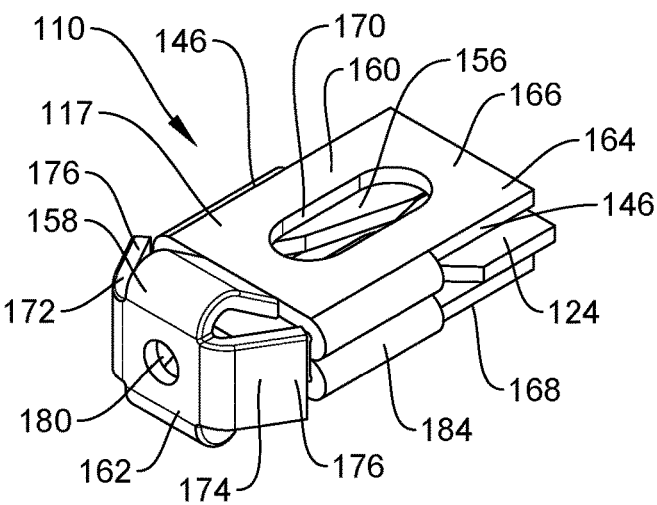
FIG. 4
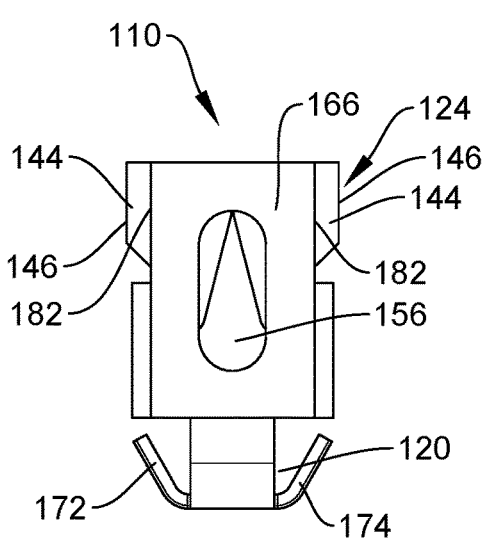
FIG. 6
FIG. 5
FIG. 7
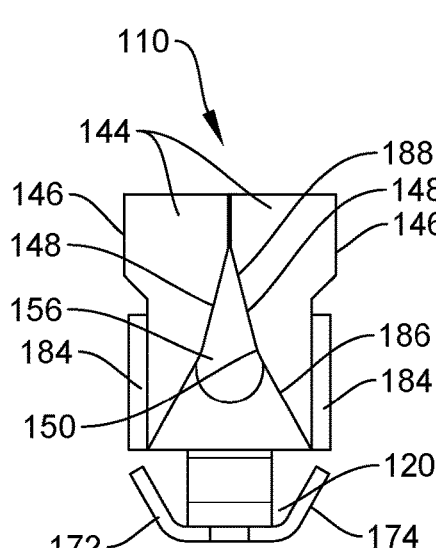

LOCKING FEATURE FOR HEMOSTASIS CLIP

PRIORITY CLAIM

The present disclosure claims priority to U.S. Provisional Patent Application Ser. No. 63/267,758 filed Feb. 9, 2022; the disclosure of which is incorporated herewith by reference.

FIELD

The present disclosure relates to endoscopic devices and, in particular, relates to endoscopic clipping devices for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, treatment of issues on other organs by passing outside of the GI tract, and endoscopic treatment/repair of post-surgical issues (e.g., post-surgical leaks, breakdown of surgical staple lines, and anastomotic leaks). Currently, tissue openings may be closed via endoscope closure devices such as, for example, hemostasis clips inserted through an endoscope. In some cases, however, current endoscopic closure devices may be difficult to use, time consuming to position, or insufficient for certain perforations, conditions, and anatomies.

SUMMARY

The present disclosure relates to embodiments a clipping system for treating tissue. The system includes a clip including a capsule extending longitudinally from a proximal end to a distal end and including a channel extending therethrough, and a pair of clip arms, proximal ends of which are slidably received within the channel to move the clip arms between an open configuration, in which distal ends of the clip arms are separated from one another to receive a tissue therebetween, and a closed configuration, in which distal ends of the clip arms are drawn toward one another to grip a tissue therebetween; a core member received between and connected to the proximal ends of the clip arms to couple the clip arms to one another, the core member including a locking feature movable between an unlocked configuration, in which the core member is slidable within the channel of the capsule, and a locked configuration, in which the locking feature engages a corresponding portion of the capsule to lock the clip arms in the closed configuration; and a control member extending through a proximal portion of the clipping system from a proximal end to an enlarged distal end housed within a proximal portion of the core member so that a longitudinal movement of the control member relative to the capsule moves the clip between the open and the closed configurations.

In an embodiment, the core member is connected to the clip arms via a connector received within holes extending through the proximal ends of the clip arms and through an elongated opening extending through the core member.

In an embodiment, the connector is slidable from a proximal end of the elongated opening to a distal end of the elongated opening to move the locking feature from the unlocked configuration to the locked configuration, the connector configured to interface with a portion of the locking feature as the connector is moved distally through the elongated opening.

In an embodiment, the core member is formed of a stamped sheet of metal sized and shaped to bent into a configuration including a proximal portion defining a cavity therewithin for housing the enlarged distal end of the control member therein and a distal portion including the locking feature.

In an embodiment, the locking feature is configured as a portion of the stamped sheet of metal bent to overlap a portion of the elongated opening of the core member to form a first and second wings which, when engaged with the connector as the connector moves distally along the elongated opening, each of which is moved radially outward to engage a corresponding locking feature of the capsule.

In an embodiment, the locking features of the capsule include a pair of windows extending through a wall thereof, the windows sized, shaped, and configured to receive therein a corresponding one of the first and second wings.

In an embodiment, the distal ends of the clip arms are biased toward the open configuration so that, when the clip arms are drawn into the capsule, the clip arms are constrained toward the closed configuration via an interior surface of the capsule and, when the clip arms are moved distally out of the capsule, the clip arms are permitted to revert to their biased open configuration.

In an embodiment, the distal end of the control member is configured to separate from a remaining length of the control member when the control member is subject to a force exceeding a predetermined threshold value to release the clip from the proximal portion of the clipping system in a clipped configuration.

In an embodiment, the core member includes a proximal opening extending through the core member in communication with the cavity so that a length of the control member extends proximally from the enlarged distal end proximally through the proximal opening, the proximal opening configured to deform to permit a proximal passage of the distal end therethrough when the control member is subject to a force exceeding a predetermined threshold value.

In addition, the present disclosure relates to a clipping system for treating tissue, which includes an insertion device extending longitudinally from a proximal end to a distal end and including a channel extending therethrough; a clip including a capsule releasably coupled to the insertion device and a pair of clip arms, the capsule extending longitudinally from a proximal end to a distal end and including a channel extending therethrough, proximal ends of the clip arms slidably received within the channel to move the clip arms between an open configuration, in which distal ends of the clip arms are separated from one another to receive a tissue therebetween, and a closed configuration, in which distal ends of the clip arms are drawn toward one another to grip a tissue therebetween; a core member received between and connected to the proximal ends of the clip arms to couple the clip arms to one another, the core member including a locking feature movable between an unlocked configuration, in which the core member is slidable within the channel of the capsule, and a locked configuration, in which the locking feature engages a corresponding portion of the capsule to lock the clip arms in the closed configuration; and a control member extending through the insertion device from a proximal end accessible to a user of the clipping system to an enlarged distal end received a proximal portion of the core member so that a longitudinal movement of the control member relative to the capsule moves the clip between the open and the closed configurations.

In an embodiment, the core member is connected to the clip arms via a connector received within holes extending through the proximal ends of the clip arms and through an elongated opening extending through the core member.

In an embodiment, the connector is slidable from a proximal end of the elongated opening to a distal end of the elongated opening to move the locking feature from the unlocked configuration to the locked configuration, the connector configured to interface with a portion of the locking feature as a pin is moved distally along the elongated opening.

In an embodiment, the core member is formed of a stamped sheet of metal sized and shaped to bent into a configuration including a proximal portion defining a cavity therewithin for housing the enlarged distal end of the control member therein and a distal portion including the locking feature.

In an embodiment, the locking feature is configured as a portion of the stamped sheet of metal bent to overlap a portion of the elongated opening of the core member to form a pair of wings which, when engaged with the connector as the connector moves distally along the elongated opening, is moved radially outward to engage the corresponding portion of the capsule.

In an embodiment, the proximal end of the capsule includes a pair of tabs crimped radially inwardly to engage a corresponding portion of a bushing at the distal end of the insertion device to releasably couple the clip to the insertion device, the core member including a pair of flaps along the proximal portion thereof which, when the core member is in the locked configuration relative to the capsule, engages the tabs of capsule to deform the tabs radially outward, out of engagement with the bushing.

Furthermore, the present disclosure relates to a method for treating target tissue, which includes inserting a clip through a working channel of an endoscope to a target site within a body via a catheter, the clip including a capsule and a pair of clip arms, proximal ends of the clip arms coupled to one another via a core member that is slidably received within the capsule; moving the clip between an open configuration and a closed configuration until a target tissue is received between distal ends of the clip arms as desired, the clip moved between the open and closed configurations via a control member coupled to the clip arms via the core member, an enlarged distal end of the core member received within a cavity defined via a proximal portion of the core member; moving the clip toward the closed configuration to grip the target tissue between the distal ends of the clip arms by drawing the control member proximally relative to the catheter; locking the clip in the closed configuration by moving a locking feature of the core member from an unlocked configuration toward a locked configuration in which the locking feature engages a corresponding portion of the capsule; and deploying the clip from the catheter by drawing the control member proximally until a force exerted on the control member exceeds a predetermined threshold value so that the enlarged distal end of the control member is separated from a remaining length thereof to release the clip from the insertion device.

In an embodiment, the core member is connected to the clip arms via a connector received within holes extending through the proximal ends of the clip arms and through an elongated opening extending through the core member.

In an embodiment, locking the clip in the closed configuration includes drawing clip arms proximally until a portion of the clip arms engage a portion of the capsule to prevent any further proximal movement of the clip arms relative to the capsule so that a further proximal movement of the control member relative to the insertion device causes the connector to slide from a proximal end of the elongated opening to a distal end of the elongated opening to move the locking feature from the unlocked configuration to the locked configuration, the connector configured to interface with a portion of the locking feature as a pin is moved distally along the elongated opening.

In an embodiment, the locking feature includes a pair of wings which overlap a portion of the elongated opening of the core member so that, when engaged with the connector as the connector moves distally along the elongated opening, the wings are moved radially outward to engage the corresponding portion of the capsule.

In an embodiment, when the locking feature is locked relative to the capsule, a pair of flaps along the proximal portion of the core member engage tabs at a proximal end of the capsule to move the tabs out of engagement with a corresponding portion of a bushing at a distal end of the catheter to release the capsule from the insertion device.

BRIEF DESCRIPTION OF THE DRAWINGS

FIG. 4 shows a perspective view of a core member according to the exemplary system of FIG. 1, in an unlocked configuration;

FIG. 5 shows a plan view of a proximal end of the core member of FIG. 4;

FIG. 6 shows a side view of the core member of FIG. 4;

FIG. 7 shows a cross-sectional view of the core member of FIG. 4, along line A-A;

DETAILED DESCRIPTION

Figure 1:
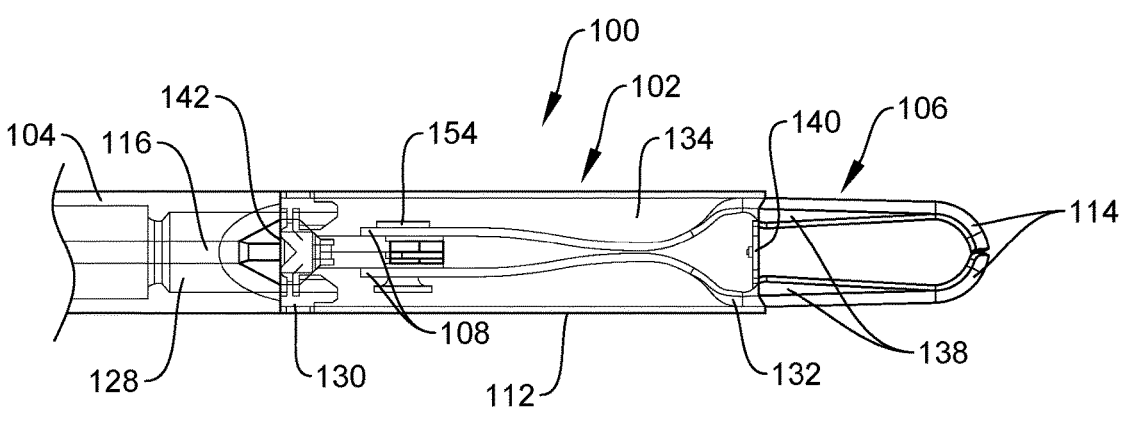
FIG. 1 shows a partially transparent longitudinal side view of a distal portion of a clipping system according to an exemplary embodiment of the present disclosure.
Figure 2:
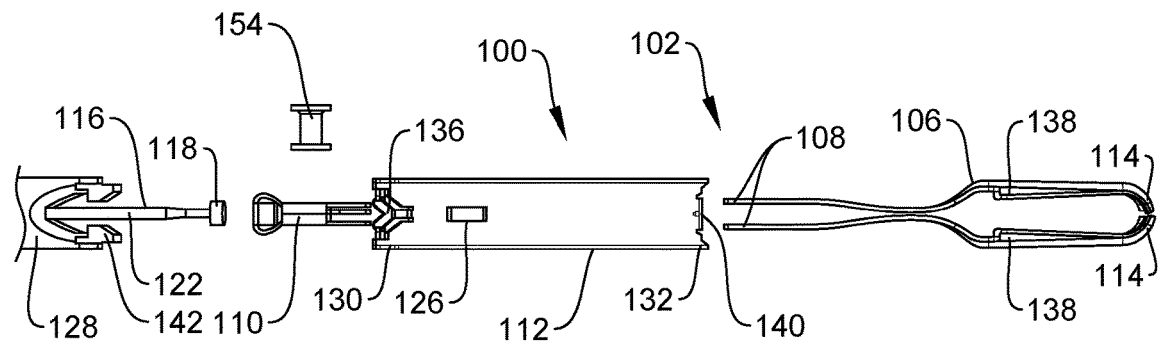
FIG. 2 shows an exploded longitudinal side view of the distal portion of the exemplary system of FIG. 1.
Figure 3:
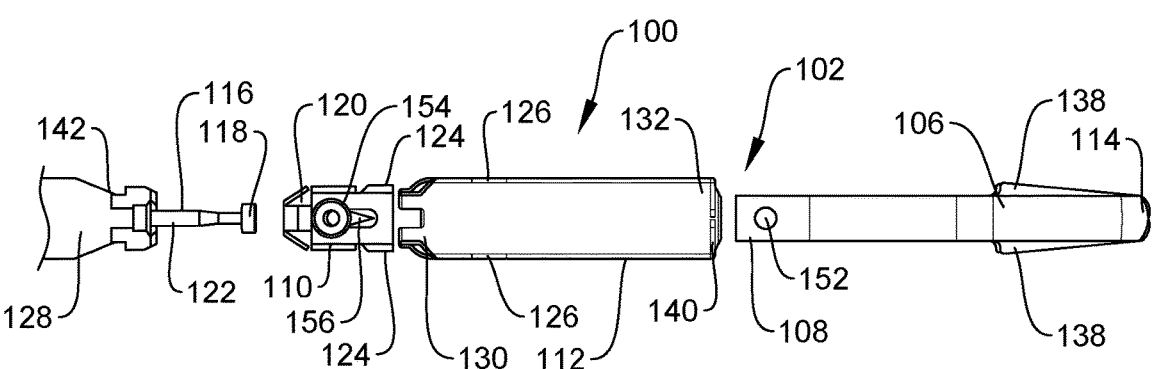
FIG. 3 shows another exploded longitudinal side view of the distal portion of the exemplary system of FIG. 2, rotated approximately 90 degrees about a longitudinal axis of the system.
Figures 8, 9:
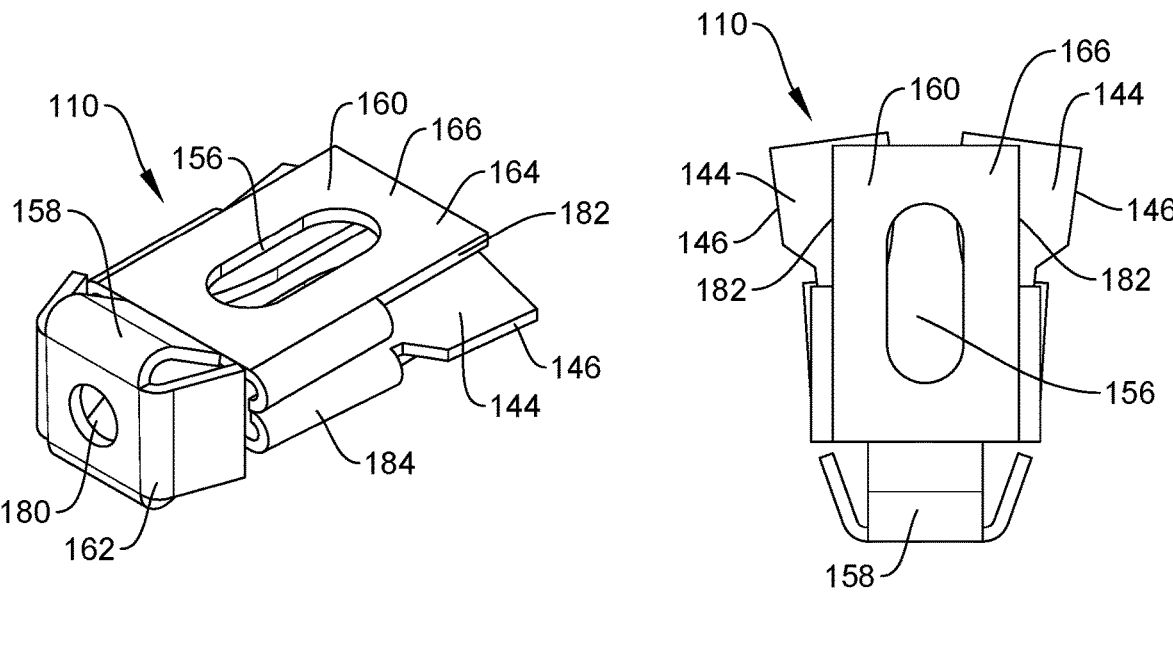
FIG. 8 shows a perspective view of the core member according to the exemplary system of FIG. 1, in a locked configuration.
FIG. 9 shows a side view of the core member of FIG. 8.

The present disclosure may be further understood with reference to the following description and the appended drawings, wherein like elements are referred to with the same reference numerals. The present disclosure is directed to an endoscopic clipping system for treating internal tissue perforations, defects and/or bleeds. Exemplary embodiments of the present disclosure describe a clipping system comprising a clip releasably coupled to a proximal portion of the system, the clip including a pair of clip arms, proximal ends of which are slidable within a capsule to move the clip arms between an open configuration, in which distal ends of the clip arms are separated from one another to receive target tissue therebetween, and a closed configuration, in which the clip arms are drawn into the capsule so that the distal ends of the clip arms are moved toward one another to grip the target tissue therebetween.

The exemplary clipping system further comprises a core member which couples the proximal ends of the clip arms to one another and to a distal end of a control member moved by an operator of the clipping system (e.g., a surgeon) to move the clip between the open and closed configurations and, upon clipping of the clip over a target tissue as desired, toward a deployment of the clip. The exemplary core member includes a locking feature or structure which, when the deployment is initiated, locks the clip arms relative to the capsule in the closed configuration. The exemplary locking feature allows the use of a capsule that is shorter reducing an overall length of a deployed clip as compared to current hemostasis clips including capsules in which a clip is locked via locking structures on the clip arms themselves.

As will be understood by those of skill in the art, shorter deployed clips may improve visualization of the target site and allow for better maneuverability when, for example, placing multiple clips. Some current clip designs also create shed parts during the deployment process of separating the clip from the catheter which shed parts may be left in the body to pass through the GI tract naturally. As the treatment of larger defect cases such as Peroral Endoscopic Myotomy (POEM) and Endoscopic Submucosal Dissection (ESD) become more prevalent, physicians may prefer clips that do not generate shed parts to eliminate the possibility of shed parts causing harm, e.g., by becoming embedded in the defects, etc.

A core member according to an exemplary embodiment is shaped or otherwise configured to eliminate shed parts by, for example, encapsulating a distal end of a control wire which separates from a remaining length of the control wire during deployment of the clip. The severed distal end of the control member remains trapped within the core member, which remains housed within the capsule of the deployed clip to contain these parts and prevent them from being shed. It will be understood by those of skill in the art that the terms proximal and distal as used herein, are intended to refer to a direction toward and away from, respectively, a user of the system.

FIGS. 1-17 show a clipping system 100 for treating tissue defects comprising a clip 102 releasably coupled to an insertion device such as, for example, a catheter 104. The clip 102 includes a pair of clip arms 106, proximal ends 108 of which are coupled to one another via a core member 110 which is slidably received within a capsule 112 to move the clip 102 between an open configuration, in which distal ends 114 of the clip arms 106 are separated from one another to receive tissue therebetween, and a closed configuration, in which the distal ends 114 of the clip arms 106 are drawn toward one another to grip tissue therebetween.

The clip arms 106 are moved between the open and closed configurations via a control member 116, a distal end 118 of which is received within a cavity 120 of the core member 110 while a reduced dimension portion 122 of the control member 116 extends proximally therefrom to pass out of the core member 110. The remaining portion of the control member 116 extends through the catheter 104, to a proximal end that is accessible to a user of the system 100 for actuation via an actuator (not shown). In this embodiment, the distal end 118 of the control member is enlarged (i.e., of increased diameter) relative to at least a portion of the control member 116 that passes through an opening in the core member 110 so that, when the control member 116 is drawn proximally, the distal end 118 pulls the core member 110 and the clip arms proximally relative to the capsule. Thus, the user may move the control member 116 longitudinally relative to the catheter 104 to move the clip 102 between the open and the closed configurations. In particular, the control member 116 may be moved distally relative to the capsule 112 to move the clip arms 106 distally out of the capsule 112 toward the open configuration and to withdraw the clip arms 106 proximally into the capsule 112 to move the clip 102 toward the closed configuration.

According to the exemplary embodiment, the core member 110 includes a locking feature 124 so that, when the clip 102 has been clipped over the target tissue as desired, deployment of the clip 102 may be initiated by drawing the control member 116 further proximally relative to the capsule 112. As will be described in further detail below, the further proximal motion of the control member 116 moves the locking feature 124 radially outward so that the locking feature 124 engages corresponding locking structures 126 of the capsule 112. Locking of the clip 102 facilitates deployment of the clip 102. In one embodiment, the control member 116 may be drawn even further proximally until a force exerted thereon until a widened portion of one or both of the clip arms 106 contacts the distal end of the capsule 112 preventing the clip arms 106 from being moved further proximally. Continued application of proximal force to the control member 116 after this point increases a tension on the control member 116. When this tension exceeds a predetermined threshold force, the distal end 118 of the control member 116 is separated from the reduced dimension portion 122 of the control member 116 releasing the clip 102 from the catheter 104. After the distal end 118 is separated from the rest of the control member 116. the distal end 118 remains trapped within the core member 110, which remains housed within the capsule 112 of the deployed clip 102. Thus, deployment of the clip 102 does not result in any shed parts.

As described above, according to an exemplary embodiment, the clipping system 100 includes the catheter 104 for inserting the clip 102 to a target area within a body. The system 100 of this embodiment includes a bushing 128 fixed to a distal end of the catheter 104 and the bushing 128 is releasably coupled to the capsule 112. The control member 116 extends through the catheter 104 and the bushing 128 so that the distal end 118 extends distally therefrom to be connected to the clip 102. It will be understood by those of skill in the art that the distal end 118 has a width in at least one dimension larger than that of the opening in the core member 110 through which the control member 116 passes through to extend proximally from the core member 110. This prevents the distal end 118 of this embodiment from passing proximally out of the opening in the core member 110. In addition, as would be understood by those skilled in the art, the separation of the distal end 118 from the rest of the control member 116 and the release of the busing 128 from the capsule 112 separates the clip 102 from the rest of the system 100 so that the clip 102 can remain in the body clipped over target tissue after the rest of the system including the catheter 104, the bushing 128 and the proximal portion of the control member 116 are withdrawn from the body.

In an exemplary embodiment, the distal end 118 is connected to the remaining length of the control member 116 (proximal portion of the control member 116) via a thinned portion, a joint or connection that is configured to release, break, or otherwise separate the distal end 118 from the reduced dimension portion 122 when subject to a force that exceeds a predetermined threshold value during the deployment process. In one example, the connection between the distal end 118 and the remaining length includes a reduced diameter portion configured to fail when subject to a force exceeding the predetermined threshold force (i.e., to fail at a force lower than a force required to break any other part of the control member 116 or to pull the distal end 118 out of the core member 110).

It will be understood by those of skill in the art, however, that the connection between the distal end 118 and the reduced dimension portion 122 of the control member 116 may have any of a variety of configurations. Additionally, although the exemplary embodiment describes the insertion device as the catheter 104, it will be understood by those of skill in the art that the insertion device may include any flexible elongate member that is insertable through, for example, tortuous paths of a body lumen to reach a target site.

The capsule 112 of the clip 102 extends from a proximal end 130 to a distal end 132 and includes a channel 134 extending therethrough. In one embodiment, the proximal end 130 is releasably coupled to the bushing 128 via, for example, one or more tabs 136 each of which is crimped radially inward to engage a corresponding engaging portion 142 of the bushing 128. The corresponding engaging portion 142 of the bushing 128 may include, for example, a groove or recess formed within the bushing 128, the groove or recess sized, shaped, or otherwise configured to engage the radially inwardly crimped tabs 136. In one embodiment, the capsule 112 includes a pair of tabs 136 diametrically opposing one another. The capsule 112 also includes locking structures 126 configured to engage the locking features 124 of the core member 110. The locking structures 126 may be formed in a capsule wall and, in one embodiment, includes windows extending laterally through the capsule wall.

Each of the clip arms 106 extends from the proximal end 108 to the distal end 114. As described above, the proximal ends 108 are slidably received within the channel 134 so that the clip arms 106 may be moved relative to the capsule 112 between the open and the closed configurations via manipulation of the control member 116. In one embodiment, the clip arms 106 are biased toward the open configuration so that, when advanced distally out of the capsule 112, the clip arms 106 move apart from one another into the open configuration under their natural bias. When the clip arms 106 are drawn proximally into the capsule 112, the clip arms 106 are constrained by the wall of the capsule 112 and drawn together toward the closed configuration, with the distal ends 114 adjacent to one another. Those skilled in the art will understand that a number of other mechanisms for opening and closing the clip arms 106 may be employed.

Each of the clip arms 106 of this embodiment also includes engaging features 138 extending therefrom configured to engage a portion of the capsule 112 so that when the engaging features 138 engage the capsule 112, the clip arms 106 are prevented from being moved further proximally into the capsule 112. In one embodiment, the engaging features 138 extend laterally outward from distal portions of the clip arms 106, so that the distal portions of the clip arms 106 have a width greater than proximal portions of the clip arms 106 and greater than a diameter of a distal opening of the capsule 112. Thus, the proximal portions of the clip arms 106 are sized to permit them to be drawn proximally into the capsule 112 while the portions of the clip arms 106 extending from the engagement features 138 distally, are too wide to be drawn into the capsule 112. Thus, as the clip arms 106 are drawn proximally into the capsule 112, the engaging features 138 abut a portion of a distal face 140 of the capsule 112 preventing further proximal movement of the clip arms 106 relative to the capsule 112. The engaging features 138 are positioned along the clip arms 106 so that, at the point where the engaging features 138 have engaged the capsule 112, the clip arms 106 have been drawn sufficiently proximally into the capsule 112 to draw the clip arms 106 together, into the closed configuration. In one example, the engaging features 138 may be configured as wings extending laterally from longitudinal edges of the clip arms 106.

Each of the proximal ends 108 of the clip arms 106, in this embodiment, includes a hole 152 extending therethrough. The hole 152 is configured to facilitate a coupling of the proximal ends 108 of the clip arms 106 with the core member 110. According to an exemplary embodiment, when the clip arms 106 are diametrically opposed relative to one another, the holes 152 of the clip arms 106 are aligned with one another so that a connector such as, for example, a rivet 154 may be passed through the holes 152 at the proximal ends 108 of the clip arms 106 and through a corresponding opening 156 of the core member 110 to couple the clip arms 106 to the core member 110.

As described above, the core member 110 is sized and configured to be longitudinally slidable within the channel 134 of the capsule 112. In an exemplary embodiment, the core member 110 is a one-piece mechanism configured to connect the control member 116 to the clip arms 106 and, according to an exemplary embodiment, is formed of a stamped sheet of material 117 (e.g., metal) sized and shaped so that, when bent as will described in further detail below, the material 117 includes a proximal portion 158 defining the cavity 120, configured to receive the distal end 118 of the control member 116, and a distal portion 160, which defines the locking feature 124 configured to lock the clip arms 106 relative to the capsule 112 in the closed configuration.

The core member 110, in the bent configuration, extends from a proximal end 162 to a distal end 164. According to an exemplary embodiment, the material 117 is bent over the proximal end 162 to include a first surface 166 and a second surface 168. A portion of the first and second surfaces 166, 168 extending along the proximal portion 158 defines the cavity 120 therebetween. A portion of the first and second surfaces 166, 168 extending along the distal portion 160 of the core member 110 may be substantially planar, extending parallel to one another and to a longitudinal axis of the capsule 112 within which the core member 110 is received in an operative configuration.

Along the distal portion 160, each of the first and second surfaces 166, 168 include an elongated opening 170 extending therethrough along a central axis. Each elongated opening 170 is elongated along a longitudinal axis of the core member 110 and are aligned relative to one another along the central axis, which extends substantially perpendicular to the first and second surfaces 166, 168. As will be described in further detail below, the elongated opening 170 of each of the first and second surfaces 166, 168 is configured to receive the rivet 154 or other connector which connects the clip arms 106 to the core member 110.

In addition to the first and second surfaces 166, 168, the core member 110 also includes a first flap 172 and a second flap 174 extending from the proximal end 162 and bent relative to the longitudinal axis of the core member 110 toward the distal end 164 to further define the cavity 120. In particular, each of the first and second flaps 172, 174 extends along the proximal portion 158 of the core member 110 so that the cavity 120 is defined between the first and second surfaces 166, 168 and the first and second flaps 172, 174. The proximal end 162 includes an opening 180 extending therethrough along a central axis that is substantially aligned with a longitudinal axis of the core member 110. The proximal opening 180 is sized and shaped so that, when the distal end 118 is received within the cavity 120, the reduced dimension portion 122 of the control member 116 passes through the proximal opening 180 to extend proximally from the enlarged distal end 118.

It will be understood by those of skill in the art that the defined cavity 120 is sized, shaped, and configured to house the enlarged distal end 118 of the control member 116 therein while the proximal opening 180 is sized and shaped to prevent the passage of the enlarged distal end 118 therethrough. No space extending between adjacent ones of the first and second flaps 172, 174 and the first and second surfaces 166, 168 is sufficient to permit the passage of the enlarged distal end 118 therethrough so that, upon deployment of the clip 102, the enlarged distal end 118 is retained housed within the cavity 120, eliminating the potential for the severed enlarged distal end 118 to escape the core member 110 thereby eliminating the risk of shed parts.

The first and second flaps 172, 174 are angled with respect to the longitudinal axis of the core member 110 so that a width of the core member 110 at the distal ends 176 (e.g., a distance between the distal ends 176) of the first and second flaps 172, 174 is greater than a width of the core member 110 at the proximal end 162 (e.g., a distance between proximal ends of the first and second flaps 172, 174). The first and second flaps 172, 174 are angled so that, when the core member 110 is drawn proximally relative to the capsule 112 during a deployment of the clip 102, the first and second flaps 172, 174 come into contact with and engage the tabs 136, which are crimped radially inwardly relative to the longitudinal capsule to 112 engage the capsule 112 with the bushing 128. As the angled surfaces of the first and second flaps 172, 174 slide proximally along the tabs 136, engagement between the first and second flaps 172, 174 and the radially inwardly crimped tabs 136 causes the tabs 136 to move radially outward relative to the longitudinal axis of the capsule 112 disengaging the tabs 136 from the corresponding engaging portion of the bushing 128.

Portions of the material 117 extending from exterior longitudinal edges 182 of one of the first surface 166 and the second surface 168 are also bent inward to extend between the first and second surfaces 166, 168 to define the locking feature 124. In an exemplary embodiment, the locking feature 124 is configured as a pair of wings 144 extending between the first and second surfaces 166, 168 and movable between an unlocked configuration and a locked configuration. In the unlocked configuration, exterior longitudinal edges 146 of the wings 144 are substantially aligned with the longitudinal edges 182 of the first surface 166 (and longitudinal edges of the second surface 168) so that the core member 110 is free to slide longitudinally within the channel 134 of the capsule 112 to move the clip arms 106 between the open and closed configurations. In the locked configuration, a portion of each of the pair of wings 144 is moved radially outward to engage the locking structures 126 of the capsule 112.

According to an exemplary embodiment, each of the wings 144 is connected to either the first surface 166 or the second surface 168 via a bent portion 184 of the material 117 extending along a proximal length of the exterior longitudinal edges 182, 146 of the one of the first and second surfaces 166, 168 and the wings 144. This bent portion 184 is deformed as the core member 110 is moved from the unlocked configuration toward the locked configuration such that a distal portion of each of the wings 144 is moved radially outward. Interior longitudinal edges 148 include a proximal portion 186 and a distal portion 188 which are angled relative to one another and relative to the longitudinal axis of the core member 110.

Each of the proximal and distal portions 186, 188 of the interior longitudinal edges 148 of the wings 144 is angled such that a width (e.g., a distance between the exterior longitudinal edge 146 and the interior longitudinal edge 148) of each of the wings 144 increases toward the distal end 162 of the core member 110. The interior longitudinal edges 148 are angled so that a portion of each of the wings 144 overlaps with the elongated openings 156. In particular, a portion of each of the wings 144 overlaps the elongated openings 156 so as not to interfere with the rivet 154, which is received within the proximal portion of the elongated openings 156 in the unlocked configuration. In one embodiment, the proximal portion 186 of the interior longitudinal edges 148 defines a portion of a space within the elongated openings 156 through which the rivet 154 is received in the unlocked configuration.

As the core member 110 is moved toward the locked configuration, the rivet 154 is moved toward the distal portion of the elongated openings 156, pressing distally against a point 150 along the interior longitudinal edges 148 at which the proximal and distal portions 186, 188 of the interior longitudinal edges 148 meet. Once the rivet 154 moves past the point 150, the rivet 154 is slid distally along and between the angled distal portions 188 of the interior longitudinal edges 148, moving the wings 144 away from one another and in a radially outward away from the longitudinal axis of the core member 110, toward the locking configuration.

Figure 10:
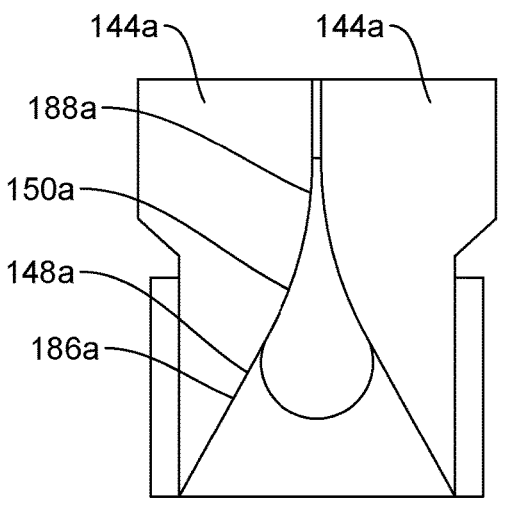
FIG. 10 shows a side view of a core member according to an alternate embodiment of the system of FIG. 1.
Figure 11:
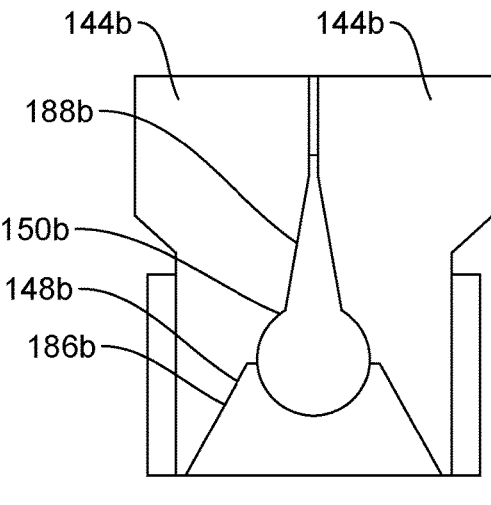
FIG. 11 shows a side view of a core member according to another alternate embodiment of the system of FIG. 1.

A force required for facilitating a deployment of the clip 102 may be adjusted, as desired, by adjusting the magnitude of the angle at which the proximal and distal portions 186, 188 of each of the interior longitudinal edges 148 of the wings 144 meet. In one example, as shown in FIG. 10, a point 150*a* at which proximal and distal portions 186*a*, 188*a* of an interior longitudinal edge 148*a* of each wing 144*a* includes a smooth curved edge decreasing a force required to deploy the clip 102. In another example, as shown in FIG. 11, an angle 150*b* at which proximal and distal portions 186*b*, 188*b* of an interior longitudinal edge 148*b* of each wing 144*b* meet is sharpened to increase the force required to deploy the clip 102. It will be understood by those of skill in the art that the force required to deploy the clip 102 may also be adjusted by adjusting a length of the bent portions 184 extending along and between the wings 144 and of the one of the first and second surfaces 166, 168 from which the wings 144 extend.

The clip 102 is assembled so that the core member 110 is received between the proximal ends 108 of the clip arms 106, the elongated openings 156 of the core member aligned with the holes 152 extending through the proximal ends 108 of the clip arms 106. The rivet 154 extends through the holes 152 of the clip arms 106 and through the proximal portion of the elongated openings 156. The core member 110 assembled with the clip arms 106 is slidably received within the channel 134 of the capsule 112. As described above, the enlarged distal end 118 of the control member 116 is housed within the cavity 120 within the proximal portion 158 of the core member 110 with the reduced dimension portion 122 extending proximally therefrom through the opening 180 at the proximal end 162 of the core member 110 and through the bushing 128 and catheter 104 to a proximal end accessible via the user or operator of the system 100.

According to an exemplary method utilizing the clipping system 100, as shown in FIGS. 12-17, the clip 102 is inserted through, for example, a working channel of an endoscope to a target site within a body. The clip 102 is inserted to the target site, in the closed configuration, via an insertion device such as the catheter 104 to which the clip 102 is releasably coupled via the bushing 128. Once the clip 102 has reached the target site, the user advances the control member 116 distally relative to the catheter 104 to move the clip arms 106 distally relative to the capsule 112 toward the open configuration.

Figure 12:
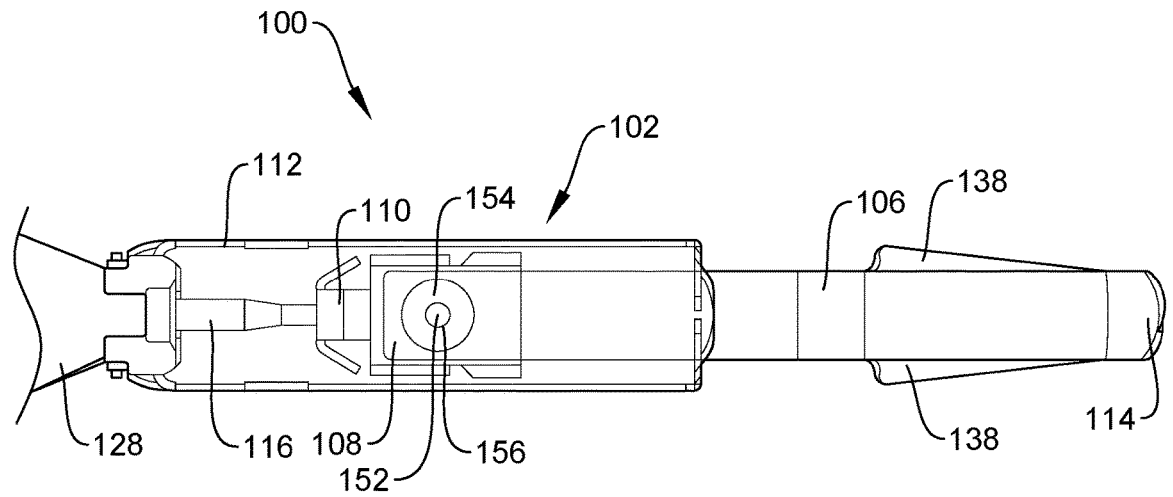
FIG. 12 shows a partially transparent longitudinal side view of a distal portion of the system of FIG. 1, in an open configuration.
Figure 13:
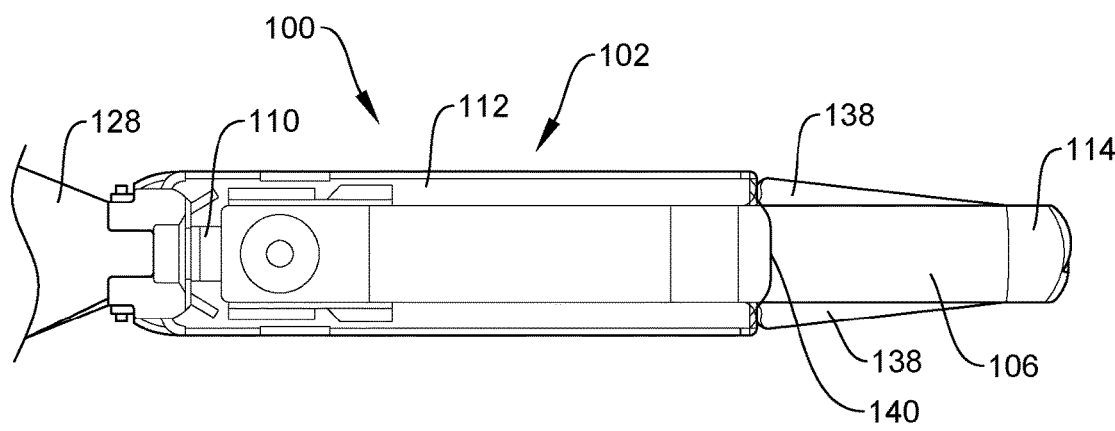
FIG. 13 shows a partially transparent longitudinal side view of a distal portion of the system of FIG. 1, in a closed configuration.
Figure 14:
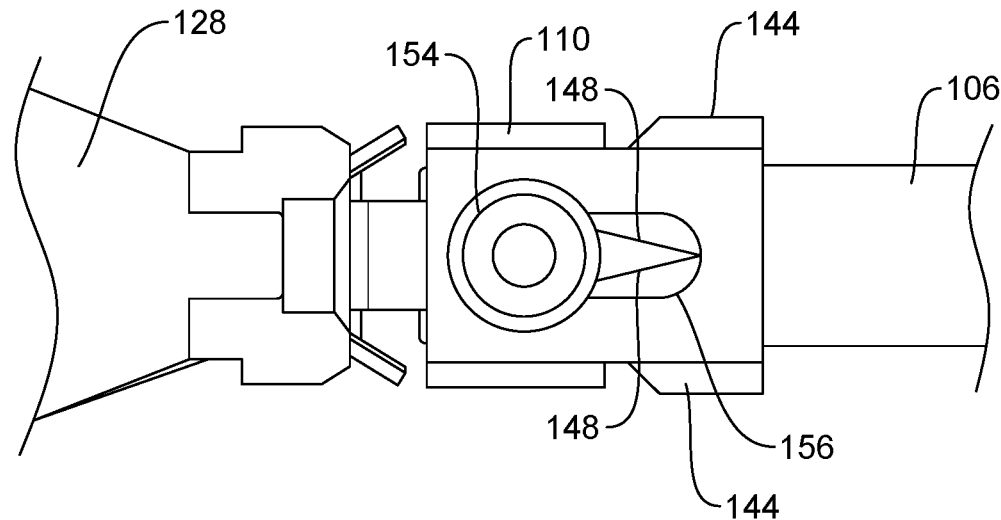
FIG. 14 shows an enlarged view of a bushing, the core member and clip arms of the system of FIG. 1, the core member in the unlocked configuration.
Figure 15:
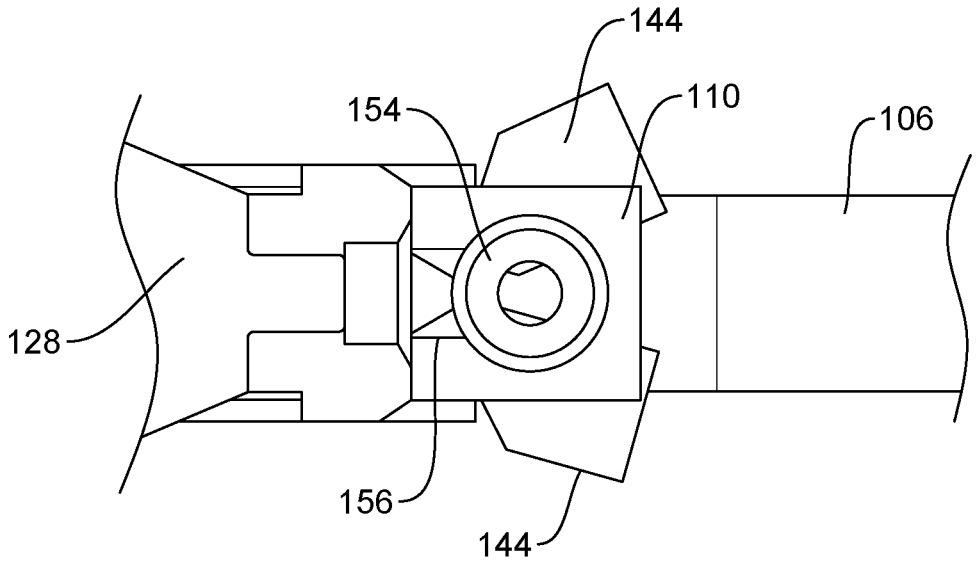
FIG. 15 shows an enlarged view of the bushing, the core member, and the clip arms of the system of FIG. 1, the core member in the locked configuration.
Figure 16:
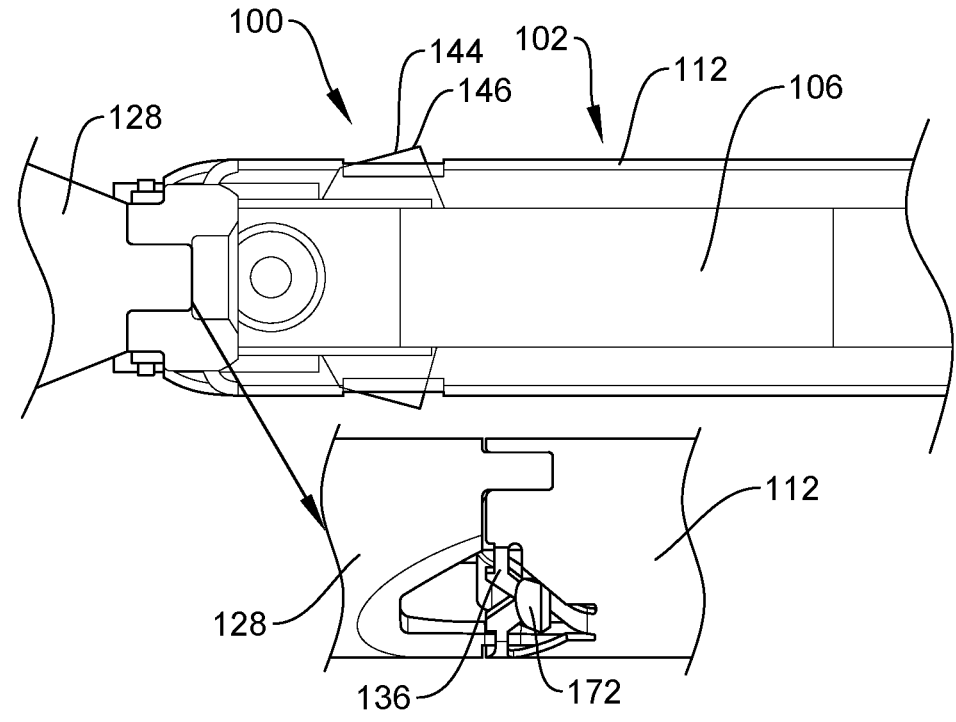
FIG. 16 shows an enlarged view of a coupling between a capsule and the bushing according to the exemplary system of FIG. 1.
Figure 17:
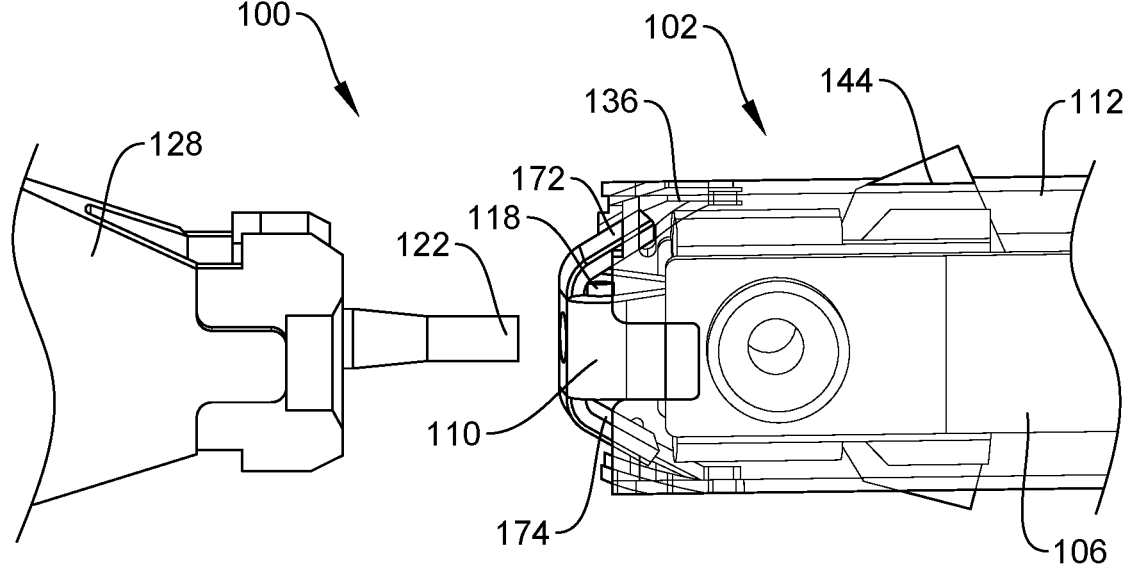
FIG. 17 shows an enlarged view of a decoupling between the capsule and the bushing, when a clip is deployed according to the exemplary system of FIG. 1.

As the clip arms 106 are extended distally from the capsule 112, the clip arms 106 move toward the open configuration, as shown in FIG. 12, under their natural bias (as they are freed from the constraints of the capsule 112) so that tissue may be received between the distal ends 114 thereof. The user may then draw the control member 116 proximally (or advance the catheter 104 distally over the control member 116) so that, as the clip arms 106 are drawn into the capsule 112, the clip arms 106 are drawn toward one another to grip the tissue received between the distal ends 114 of the clip arms 106. The clip 102 may be moved between the open and closed configurations, as desired, until a target portion of the tissue is positioned between the clip arms 106 as desired.

When the user is satisfied that the clip 102 is in a desired position gripping the target tissue, the user may deploy the clip 102 to lock the clip 102 in the closed configuration and release the clip 102 from the catheter 104. According to an exemplary embodiment, the user draws the control member 116 proximally so that the engaging features 138 of the clip arms 106 engage the distal face 140 of the capsule 112, preventing a further proximal motion of the clip arms 106 relative to the capsule 112. After this point, continued proximal motion of the control member 116, draws the core member 110 proximally relative to the clip arms 106, the rivet 154 received within the openings 156 of the clip arms 106, and the capsule 112. This causes the core member 110 to slide proximally over the rivet 154 which moves from its position in the proximal portions of the elongated openings 156 of the core member 110 toward the distal portions of the elongated openings 156.

As the rivet 154 slides toward the distal portion of the elongated openings 156, the rivet 154 engages portions of the wings 144 overlapping the elongated openings 156. The rivet 154 slides distally along the angled interior longitudinal edges 148 of the wings 144 pushing the wings 144 from the unlocked configuration radially outward toward the locked configuration. In the locked configuration, the wings 144 are moved radially outward relative to the longitudinal axis of the core member 110 to engage the locking structures 126 (e.g., the wings 144 extend into and/or through windows) extending along the capsule wall.

The core member 110 is configured so that when the wings 144 of the locking feature 124 of the core member 110 are in the locked configuration, the proximal portion 158 of the core member 110 is received within the proximal end 130 of the capsule 112 so that the first and second flaps 172, 174 engage the radially inwardly crimped tabs 136 of the capsule 112, forcing the tabs 136 radially outward, out of engagement with the bushing 128. Thus, once the core member 110 is locked with respect to the capsule 112, to finally deploy the clip 102, the user my continue to draw the control member 116 proximally until the force exerted therealong exceeds the predetermined threshold value, causing the enlarged distal end 118 to separate from the remaining length of the control member 116. The catheter 104 and the reduced dimension portion 122 of the control member 116 may then be withdrawn from the body, leaving the clip 102 deployed within the body, gripped over the target tissue.

Figure 18:
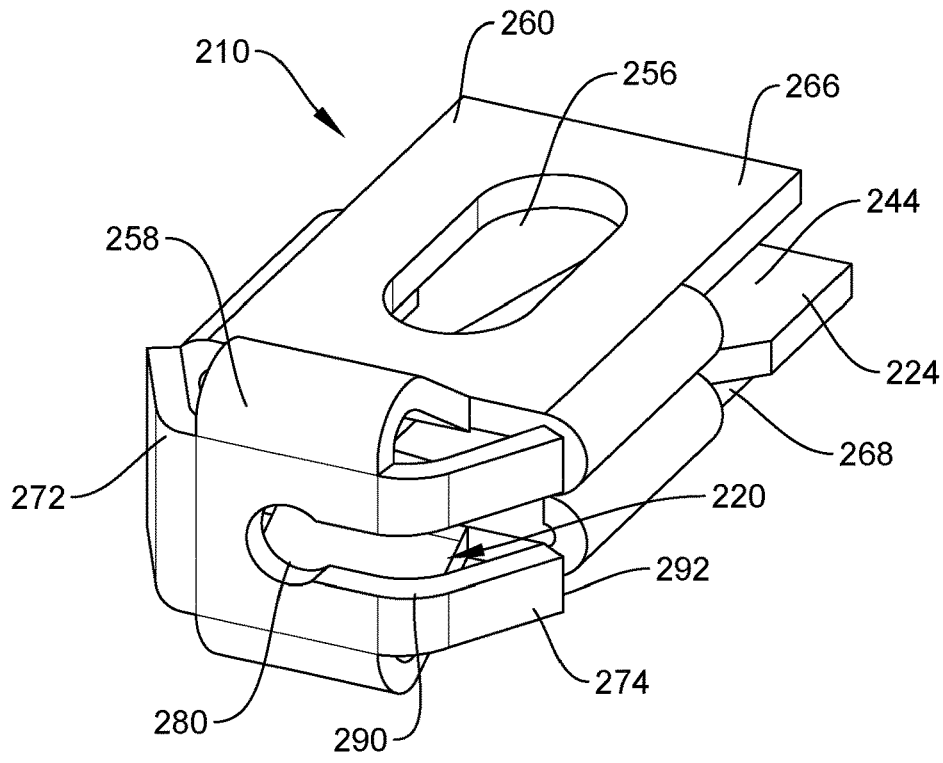
FIG. 18 shows a perspective view of a core member according to another exemplary embodiment of the present disclosure.

As shown in FIG. 18, a core member 210 according to another exemplary embodiment of the present disclosure may be substantially similar to the core member 110, as described above with respect to the clipping system 100, comprising a proximal portion 258 defining a cavity 220, within which the enlarged distal end 118 of the control member 116 may be received, and a distal portion 260 including a locking feature 224 such as, for example, wings 244 received between a first surface 266 and a second surface 268 of the core member 110. The distal portion 260 may be substantially similar to the distal portion 160 of the core member 110, including substantially similar features and functioning substantially similarly to the core member 110.

The proximal portion 258 may also be substantially similar to the proximal portion 158 of the core member 110, the cavity 220 being defined via proximal portions of the first and second surfaces 266, 268 and via first and second flaps 272, 274. One of the first and second flaps 272, 274 in the embodiment, however, includes a slot 290 extending therealong so that a proximal opening 280 extending through a proximal end 262 of the core member 210 is open to an edge 292 of the one of the first and second flaps 272, 274. The slot 290 is sized, shaped, and configured to facilitate an assembly of the control member 116 with the core member 210. In particular, a portion of the control member 116 immediately proximal the enlarged distal end 118 may be slid along the slot 290 so that the enlarged distal end 118 may be passed into the cavity 220, with the reduced dimension portion 122 of the control member 116 extends proximally therefrom through the proximal opening 280.

In one embodiment, during deployment, the enlarged distal end 118 may separate from the reduced dimension portion 122 when a force exerted thereon exceeds a predetermined threshold force so that the enlarged distal end 118 remains housed within the cavity 220. In another embodiment, during deployment, when a force exerted on the proximal end 262 exceeds the predetermined threshold value, the portions of the one of the first and second flaps 272, 274 defined via the slot 290 are deformed away from one another, increasing a size of the proximal opening 280 so that the enlarged distal end 118 may pass proximally therethrough.

Figure 19:
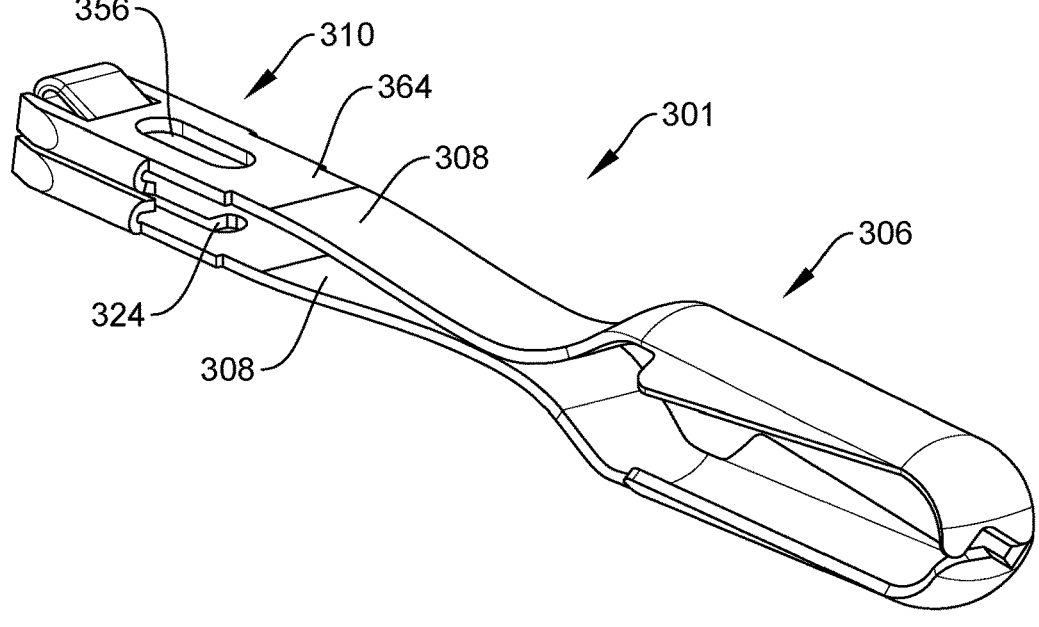
FIG. 19 shows a perspective view of an integrally formed core member and clip arms according to yet another exemplary embodiment of the present disclosure.

According to yet another exemplary embodiment, as shown in FIG. 19, clip arms 306 are integrally formed with a core member 310 so that the clip arms 306 and the core member 310 form a single component 301. The clip arms 306 and the core member 310 may be substantially similar to the clip arms 106 and core member 110 described above with respect to the clipping system 100. In this embodiment, however, proximal ends 308 of the clip arms 306 are directly connected to the core member 310 (e.g., at a distal end 364 of the core member 310). Since a rivet is not required to connect the proximal ends 308 of the clip arms 306 with the core member 310, in this embodiment, a pin or rivet may be received with a distal portion of the elongated openings 356 of the core member 310 in the unlocked configuration and slid toward a proximal portion of the elongated openings 356 in the locked configuration. The pin or rivet may be attached to a distal end of a control member, which extends through a proximal opening of the core member 310, substantially as described above with respect to the system 100.

During deployment of a clip according to this embodiment, the control member (and the pin or rivet received within the elongated openings 356) is drawn proximally relative to the clip arms 306 to move the core member 310 from the unlocked to the locked configuration. It will be understood by those of skill in the art that the locking feature 324 of the core member 310 may simply be inverted relative to the locking feature 124 described above with respect to the system 100. For example, portions of wings of the locking feature 324 may overlap with a proximal portion of the elongated openings 356.

Figure 20:
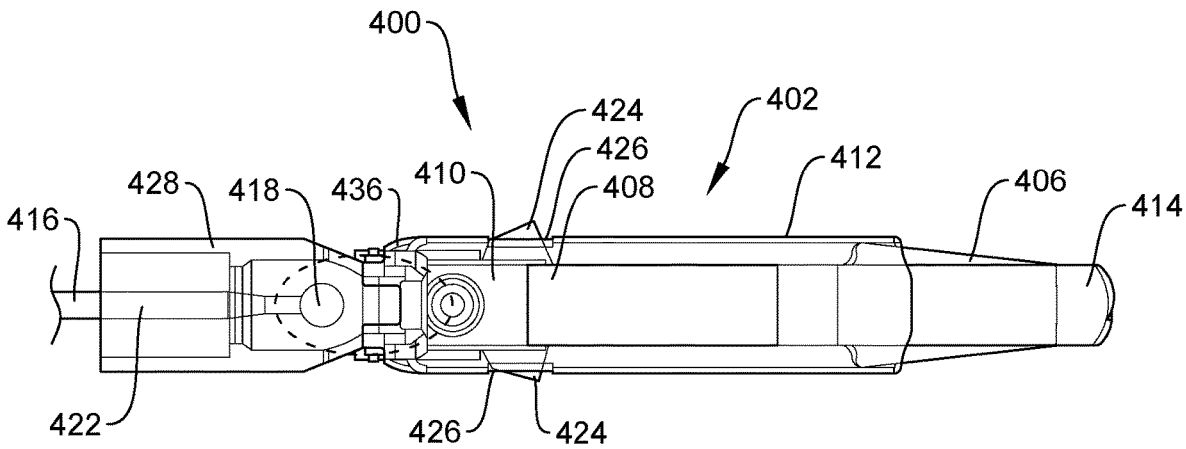
FIG. 20 shows a partially transparent longitudinal side view of a distal portion of a system according to another exemplary embodiment of the present disclosure.
Figure 21:
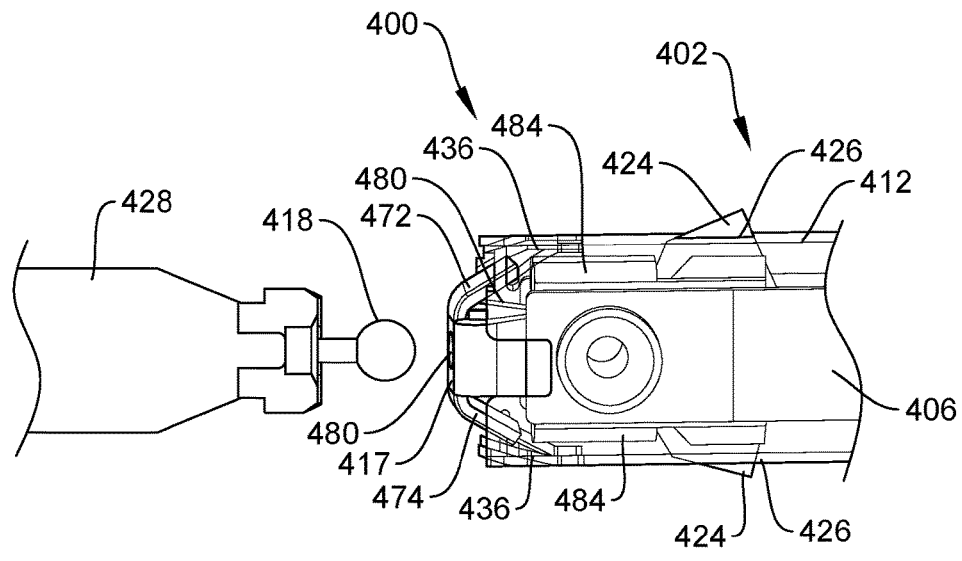
FIG. 21 shows an enlarged longitudinal side view of a control member separated from a clip during a deployment process, according to the system of FIG. 20.
Figures 22A, 22B:
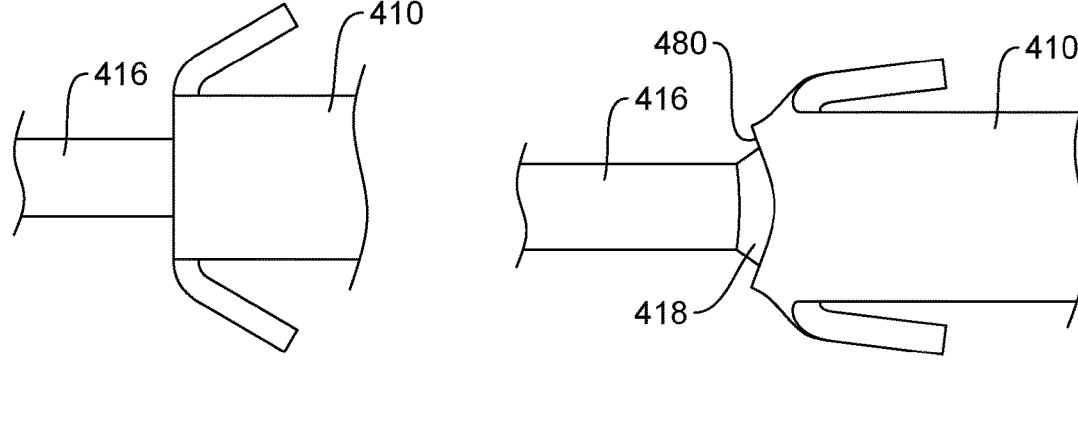
FIGS. 22*a*-22*d* show a schematic sequence of images showing a deformation of a proximal opening of a core member according to the system of FIG. 20.
Figures 22C, 22D:
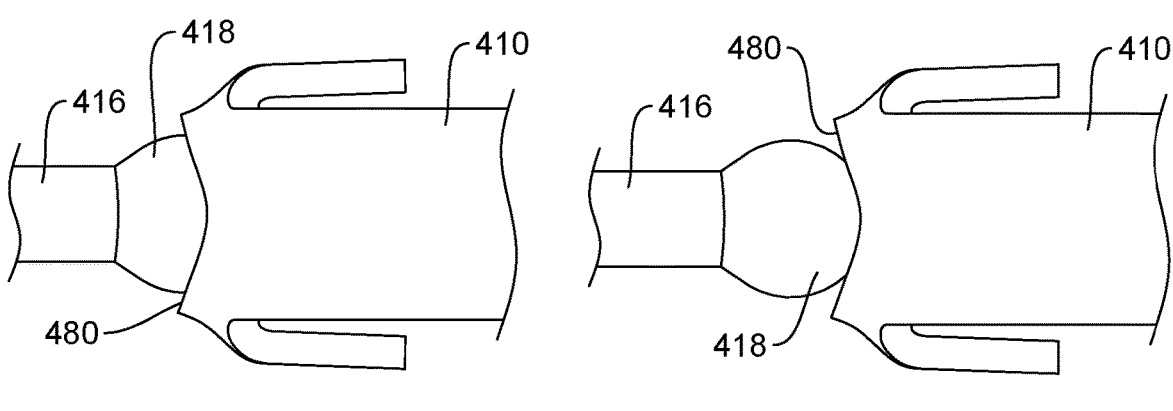

As shown in FIGS. 20-22, a system 400 according to another exemplary embodiment of the present disclosure may be substantially similar to the system 100 described above, comprising a clip 402 releasably coupled to an insertion device such as, for example, a catheter (not shown), via a bushing 428. Similarly to the clip 102, the clip 402, as shown in FIG. 20, includes a pair of clip arms 406, proximal ends 408 of which are coupled to one another via a core member 410, which is slidably received within a capsule 412 to move the clip 402 between an open configuration, in which distal ends 414 of the clip arms 406 are separated from one another to receive a tissue therebetween, and a closed configuration, in which the distal ends 414 of the clip arms 406 are drawn toward one another to grip tissue therebetween. The clip 402 is moved between the open and the closed configurations via a control member 416, an enlarged distal end 418 of which is received within a cavity 420 of the core member 410. The clip 402, the control member 416, and the core member 410, in this embodiment, may be substantially similar to the clip 102, the control member 116, and the core member 110 (or core members 210, 310), as described above, and may be utilized in a manner substantially similar to the system 100. As will be described in further detail below, however, the enlarged distal end 418, in this embodiment, does not separate from a remaining portion of the control member 416 during a deployment process. Rather, during deployment, the enlarged distal end 418 of the control member 416 is draw proximally against a proximal opening 480 of the core member 410 until the proximal opening 480 deforms to permit a proximal passage of the enlarged distal end 418 therethrough, thereby separating the control member 416 from the clip 402.

Similarly to the clip 102, the clip 402 is moved between the open and the closed configurations until a target tissue is clipped, as desired. In particular, the control member 416 is moved distally relative to the capsule 412 to move the clip arms 406 toward the open configuration and proximally relative to the capsule 412 to move the clip arms 406 toward the closed configuration. Upon clipping of the target tissue, the clip 402 may be locked in the closed configuration by drawing the control member 416 further proximally relative to the capsule 412 until locking features 424 (e.g., wings) of the core member 410 engage corresponding locking structures 426 (e.g., windows) of the capsule 412. As described above with respect to the system 100, this further proximal motion of the control member 416 relative to the capsule 410 causes the locking features 424 to move in a radially outward direction so that the locking features 424 engage the corresponding locking structures 426 of the capsule 412 (shown in FIGS. 20-21). According to an embodiment, when the locking features 424 engage the corresponding locking structures 426, first and second flaps 472, 474 along a proximal portion 458 of the core member 410 engage radially inwardly crimped tabs 436 of the capsule 412, forcing the tabs 436 out of engagement with the bushing 428, which connects the clip 402 to the insertion device. Thus, once the core member 410 is locked with respect to the capsule 412, to finally deploy the clip 402, the user may continue to draw the control member 416 proximally relative to the capsule 412 until the force exerted therealong exceeds a predetermined threshold value, causing the control member 416 to separate from the clip 402, as shown in FIG. 20. The user may then withdraw the insertion device and control member 416 from the body, as shown in FIG. 21, leaving the deployed clip 402.

In this embodiment, however, the proximal opening 480 of the core member 410, through which a remaining length 422 of the control member 416 extends when the enlarged distal end 418 is received within the cavity 420, is configured to deform when subject to a force exceeding the predetermined threshold value. In particular, the proximal opening 480 is deformed to permit the proximal passage of the enlarged distal end 418 therethrough so that the control member 416 remains intact during deployment. According to an exemplary embodiment, a thickness of a portion of a material 417 surrounding the proximal opening 480 may be selected to facilitate a deformation thereof, as the enlarged distal end 418 is drawn proximally thereagainst. As shown in the sequence of images in FIGS. 22a-22d, the control member 416 is drawn proximally relative to the control member 410 so that the enlarged distal end 418 continues to apply a force exceeding the predetermined threshold force on the proximal opening 480 and, in particular, along a portion of the material 417 surrounding the proximal opening 480, until the proximal opening 480 is sufficiently deformed to permit passage of the entire enlarged distal end 418 therethrough. Thus, once the enlarged distal end 418 passes through the deformed proximal opening 480, the insertion device and the control member 416 may be separated from the clip 402 and removed from the body, leaving the deployed clip 402 clipped over the target tissue in the body. As there are no broken and/or separated pieces during deployment, it will be understood by those of skill in the art that this embodiment also does not create any shed parts and thus eliminates the risks thereof.

Although the exemplary embodiment shows and describes the core member 410 as including first and second flaps 472, 474 configured to engage a portion of the capsule 412 to release the bushing 428 therefrom, in another embodiment, the first and second flaps 472, 474 may be eliminated. As discussed above with respect to the system 100, the first and second flaps 472, 474 facilitate housing of the enlarged distal end 418 within the cavity 420. Since the enlarged distal end 418 of the system 400, however, is not separated from the remaining length 422 of the control member 416 during deployment, the flaps 472, 474 may be eliminated as they are not required to prevent escape of the enlarged distal end 418 after deployment. In this embodiment, bent portions 484 of the core member 410, which connect the locking features 424 to a surface of the core member 410, may be configured to engage the crimped tabs 436 of the capsule 412 during a deployment process. Similarly to the core member 110, as described above with respect to the system 100, these bent portions 484 deform as the locking features 424 are moved toward the locking configuration. In this embodiment, the bent portions 484 are configured so that, as they are deformed when the core member 410 moves from the unlocked configuration to the locked configuration, the bent portions 484 engage the radially inwardly crimped tabs 436 of the capsule 412, forcing the tabs 436 radially outward, out of engagement with the bushing 428.

It will be apparent to those skilled in the art that various modifications may be made in the present disclosure, without departing from the scope of the disclosure. Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

What is claimed is:

1. A clipping system for treating tissue, comprising:
a clip including a capsule extending longitudinally from a proximal end to a distal end and including a channel extending therethrough, and a pair of clip arms, proximal ends of which are slidably received within the channel to move the clip arms between an open configuration, in which distal ends of the clip arms are separated from one another to receive a tissue therebetween, and a closed configuration, in which distal ends of the clip arms are drawn toward one another to grip a tissue therebetween;
a core member received between and connected to the proximal ends of the clip arms to couple the clip arms to one another, the core member including a proximal portion and a distal portion, the distal portion including a lock movable between an unlocked configuration, in which the core member is slidable within the channel of the capsule, and a locked configuration, in which the lock is moved away from a longitudinal axis of the control member toward a radially outward position such that the lock engages a corresponding portion of the capsule to lock the clip arms in the closed configuration; and
a control member extending longitudinally from a proximal end accessible to a user to an enlarged distal end, the enlarged distal end of the control member housed within the proximal portion of the core member so that a longitudinal movement of the control member relative to the capsule moves the clip between the open and the closed configurations.

2. The system of claim 1, wherein the core member is connected to the clip arms via a connector received within holes extending through the proximal ends of the clip arms and through an elongated opening extending through the core member.

3. The system of claim 2, wherein the connector is slidable from a proximal end of the elongated opening to a distal end of the elongated opening to move the lock from the unlocked configuration to the locked configuration, the connector configured to interface with a portion of the lock as the connector is moved distally through the elongated opening.

4. The system of claim 2, wherein the core member is formed of a stamped sheet of metal sized and shaped so that it is bent into a configuration including the proximal portion, which defines a cavity therewithin for housing the enlarged distal end of the control member therein, and the distal portion including the lock.

5. The system of claim 4, wherein the lock is configured as a portion of the stamped sheet of metal bent to overlap a portion of the elongated opening of the core member to form first and second wings which, when engaged with the connector as the connector moves distally along the elongated opening, are moved radially outward to engage a corresponding locking feature of the capsule.

6. The system of claim 5, wherein the locking features of the capsule include a pair of windows extending through a wall thereof, the windows sized, shaped, and configured to receive therein a corresponding one of the first and second wings.

7. The system of claim 1, wherein the distal ends of the clip arms are biased toward the open configuration so that, when the clip arms are drawn into the capsule, the clip arms are constrained toward the closed configuration via an interior surface of the capsule and, when the clip arms are moved distally out of the capsule, the clip arms are permitted to revert to their biased open configuration.

8. The system of claim 1, wherein the distal end of the control member is configured to separate from a remaining length of the control member when the control member is subject to a force exceeding a predetermined threshold value to release the clip from the proximal portion of the clipping system in a clipped configuration.

9. The system of claim 4, wherein the core member includes a proximal opening extending through the core member in communication with the cavity so that a length of the control member extends proximally from the enlarged distal end proximally through the proximal opening, the proximal opening configured to deform to permit a proximal passage of the distal end therethrough when the control member is subject to a force exceeding a predetermined threshold value.

10. A clipping system for treating tissue, comprising:

an insertion device extending longitudinally from a proximal end to a distal end and including a channel extending therethrough;

a clip including a capsule releasably coupled to the insertion device and a pair of clip arms, the capsule extending longitudinally from a proximal end to a distal end and including a channel extending therethrough, proximal ends of the clip arms slidably received within the channel to move the clip arms between an open configuration, in which distal ends of the clip arms are separated from one another to receive a tissue therebetween, and a closed configuration, in which distal ends of the clip arms are drawn toward one another to grip a tissue therebetween;

a core member received between and connected to the proximal ends of the clip arms to couple the clip arms to one another, the core member including a proximal portion and a distal portion, the distal portion including a lock movable between an unlocked configuration, in which the core member is slidable within the channel of the capsule, and a locked configuration, in which the lock is moved away from a longitudinal axis of the core member toward a radially outward position to engage a corresponding portion of the capsule to lock the clip arms in the closed configuration; and a control member extending longitudinally through the insertion device from a proximal end accessible to a user of the clipping system to an enlarged distal end received within the proximal portion of the core member so that a longitudinal movement of the control member relative to the capsule moves the clip between the open and the closed configurations.

11. The system of claim 10, wherein the core member is connected to the clip arms via a connector received within holes extending through the proximal ends of the clip arms and through an elongated opening extending through the core member.

12. The system of claim 11, wherein the connector is slidable from a proximal end of the elongated opening to a distal end of the elongated opening to move the lock from the unlocked configuration to the locked configuration, the connector configured to interface with a portion of the lock as a pin is moved distally along the elongated opening.

13. The system of claim 12, wherein the core member is formed of a stamped sheet of metal sized and shaped to bent into a configuration including the proximal portion, which defines a cavity therewithin for housing the enlarged distal end of the control member therein, and the distal portion including the lock.

14. The system of claim 13, wherein the lock is configured as a portion of the stamped sheet of metal bent to overlap a portion of the elongated opening of the core member to form a pair of wings which, when engaged with the connector as the connector moves distally along the elongated opening, is moved radially outward to engage the corresponding portion of the capsule.

15. The system of claim 11, wherein the proximal end of the capsule includes a pair of tabs crimped radially inwardly to engage a corresponding portion of a bushing at the distal end of the insertion device to releasably couple the clip to the insertion device, the core member including a pair of flaps along the proximal portion thereof which, when the core member is in the locked configuration relative to the capsule, engages the tabs of capsule to deform the tabs radially outward, out of engagement with the bushing.

16. A method for treating target tissue, comprising:

inserting a clip through a working channel of an endoscope to a target site within a body via a catheter, the clip including a capsule and a pair of clip arms, proximal ends of the clip arms coupled to one another via a core member that is slidably received within the capsule;

moving the clip between an open configuration and a closed configuration until a target tissue is received between distal ends of the clip arms as desired, the clip moved between the open and closed configurations via a control member coupled to the clip arms via the core member, an enlarged distal end of the control member received within a cavity defined via a proximal portion of the core member, a remaining length of the control member extending proximally from the enlarged distal end, longitudinally through the catheter, toward a proximal end accessible to a user so that a longitudinal movement of the control member relative to the catheter moves the clip between the open and the closed configurations;

moving the clip toward the closed configuration to grip the target tissue between the distal ends of the clip arms by drawing the control member proximally relative to the catheter;

locking the clip in the closed configuration by moving a lock of the core member from an unlocked configuration toward a locked configuration, in which the lock is moved radially outward to engage a corresponding portion of the capsule; and deploying the clip from the catheter by drawing the control member proximally until a force exerted on the control member exceeds a predetermined threshold value so that the enlarged distal end of the control member is separated from a remaining length thereof to release the clip from an insertion device.

17. The method of claim 16, wherein the core member is connected to the clip arms via a connector received within holes extending through the proximal ends of the clip arms and through an elongated opening extending through the core member.

18. The method of claim 17, wherein locking the clip in the closed configuration includes drawing clip arms proximally until a portion of the clip arms engage a portion of the capsule to prevent any further proximal movement of the clip arms relative to the capsule so that a further proximal movement of the control member relative to the insertion device causes the connector to slide from a proximal end of the elongated opening to a distal end of the elongated opening to move the lock from the unlocked configuration to the locked configuration, the connector configured to interface with a portion of the lock as a pin is moved distally along the elongated opening.

19. The method of claim 18, wherein the lock includes a pair of wings which overlap a portion of the elongated opening of the core member so that, when engaged with the connector as the connector moves distally along the elongated opening, the wings are moved radially outward to engage the corresponding portion of the capsule.

20. The method of claim 16, wherein when the lock is locked relative to the capsule, a pair of flaps along the proximal portion of the core member engage tabs at a proximal end of the capsule to move the tabs out of engagement with a corresponding portion of a bushing at a distal end of the catheter to release the capsule from the insertion device.

* * * * *